US010314679B2

(12) United States Patent
Blank et al.

(10) Patent No.: US 10,314,679 B2
(45) Date of Patent: Jun. 11, 2019

(54) HANDS-FREE ORAL CARE DEVICE AND METHOD (71) Applicants: Andrew Blank, Hudson, MA (US); Jeffrey Freedman, Cumming, GA (US)

(72) Inventors: Andrew Blank, Hudson, MA (US); Jeffrey Freedman, Cumming, GA (US)

( * ) Notice: Subject to any disclaimer, the term of this patent is extended or adjusted under 35 U.S.C. 154(b) by 76 days.

(21) Appl. No.: 15/207,499

(22) Filed: Jul. 11, 2016

(65) Prior Publication Data
US 2017/0007383 A1 Jan. 12, 2017

Related U.S. Application Data (60) Provisional application No. 62/190,409, filed on Jul. 9, 2015.

(51) Int. Cl.
*A61C 17/22* (2006.01)
*A61C 17/34* (2006.01)
(Continued)

(52) U.S. Cl.
CPC ........ *A61C 17/228* (2013.01); *A46B 15/0012* (2013.01); *A61C 17/349* (2013.01);
(Continued)

(58) Field of Classification Search
CPC . A61C 17/228; A61C 17/3481; A61C 17/349; A46B 15/0012
See application file for complete search history.

(56) References Cited

U.S. PATENT DOCUMENTS 3,769,652 A  11/1973 Rainer
4,011,616 A  3/1977 Kennedy
(Continued)

FOREIGN PATENT DOCUMENTS

WO  2004/108008 A1  12/2004
WO  2013/041743 A1  3/2013

OTHER PUBLICATIONS

[No Author Listed] K-12 students look ahead to a brighter future! 15th Annual Toshiba/NSTA ExploraVision Program Announces 2007 Student Winners. Business Wire: A Berkshire Hathaway Company, May 10, 2007, 7 pages. Retrieved from <http://www.businesswire.com/news/home/20070510005859/en/K-12-Students-Brighter-Future> on Oct. 18, 2016.
(Continued)

*Primary Examiner* — Laura C Guidotti
(74) *Attorney, Agent, or Firm* — Nutter McClennen & Fish LLP (57) ABSTRACT

Hands-free oral care devices and methods are described herein. In one embodiment, an oral care device includes a mouthpiece configured to be received within a user's mouth, the mouthpiece including an upper bristle track and a lower bristle track that are pivotably coupled together. The device further includes a first housing component coupled to the mouthpiece such that at least a portion of the first housing component can be compressed between the upper bristle track and the lower bristle track, and a second housing component sealingly coupled to the first housing component to define a watertight cavity therebetween. A battery can be disposed within the cavity, as well as an actuator and a pressure sensitive switch that is effective to detect pressure exerted on the first housing component when the upper and lower bristle tracks pivotably move relative to one another and selectively couple the actuator to the battery.

6 Claims, 4 Drawing Sheets (51) Int. Cl.
*A46B 15/00* (2006.01)
*A46B 9/04* (2006.01)
(52) U.S. Cl.
CPC .......... *A61C 17/3481* (2013.01); *A46B 9/045* (2013.01); *A61C 17/221* (2013.01)

(56) References Cited

U.S. PATENT DOCUMENTS

| | | | |
|---|---|---|---|
| 4,224,710 | A | 9/1980 | Solow |
| 4,237,574 | A | 12/1980 | Kelly et al. |
| 5,104,315 | A | 4/1992 | McKinley |
| 5,175,901 | A | 1/1993 | Rabinowitz |
| 5,177,827 | A | 1/1993 | Ellison |
| 6,223,376 | B1 | 5/2001 | Lee |
| 6,353,956 | B1 | 3/2002 | Berge |
| 6,893,259 | B1 | 5/2005 | Reizenson |
| 7,082,638 | B2 | 8/2006 | Koh |
| 8,161,591 | B2 * | 4/2012 | Gatzemeyer ............. A46B 5/00 15/143.1 |
| 8,292,624 | B2 | 10/2012 | Gallagher, Jr. et al. |
| 8,448,282 | B2 | 5/2013 | Stapelbroek et al. |
| 8,631,531 | B2 | 1/2014 | Garner et al. |
| 8,635,731 | B2 | 1/2014 | Garner et al. |
| 8,684,956 | B2 | 4/2014 | McDonough et al. |
| 8,745,802 | B2 | 6/2014 | Steur |
| 8,863,346 | B2 | 10/2014 | Headstrom et al. |
| 8,978,189 | B1 | 3/2015 | Sexton |
| 9,277,980 | B2 | 3/2016 | Leveling et al. |
| D764,061 | S | 8/2016 | Furdui-Carr |
| D781,427 | S | 3/2017 | Blank et al. |
| 2005/0125918 | A1 | 6/2005 | Brooks |
| 2009/0208898 | A1 | 8/2009 | Kaplan |
| 2009/0276972 | A1 | 11/2009 | Dugan |
| 2011/0072605 | A1 | 3/2011 | Steur |
| 2011/0154595 | A1 | 6/2011 | Hill |
| 2011/0252590 | A1 | 10/2011 | Steur |
| 2011/0289709 | A1 | 12/2011 | Attaway |
| 2012/0260441 | A1 | 10/2012 | Miller et al. |
| 2013/0014332 | A1 | 1/2013 | Garner et al. |
| 2013/0067665 | A1 | 3/2013 | Sowinski |
| 2013/0220357 | A1 | 8/2013 | Campbell |
| 2014/0093836 | A1 | 4/2014 | Wolpo |
| 2014/0272761 | A1 * | 9/2014 | Lowe .................. A61C 17/005 433/24 |
| 2015/0250571 | A1 | 9/2015 | Oelgiesser |
| 2015/0282910 | A1 | 10/2015 | Furdui-Carr |

OTHER PUBLICATIONS

Molina, B., Blizzident toothbrush cleans teeth in 6 seconds. USA Today, Oct. 3, 2013, 2 pages. Retrieved from <http://www.usatoday.com/story/tech/2013/10/03/blizzident-toothbrush/2914395> on Oct. 18, 2016.

Simielli, F., et al., Mouthguard toothbrush. The Enthusiastic Engineers, Penn State University, 2011, 9 pages. Retrieved from <http://www.personal.psu.edu/users/j/x/jxz5107/project%201.html> on Oct. 18, 2016.

* cited by examiner

HANDS-FREE ORAL CARE DEVICE AND METHOD

CROSS-REFERENCE TO RELATED APPLICATIONS

This disclosure claims the benefit of U.S. Provisional Application No. 62/190,409, entitled "Hands-free Oral Care Device and Method," and filed Jul. 9, 2015. The entire contents of this application are incorporated by reference herein.

FIELD

This invention relates generally to oral care, and more particularly to hands-free devices and methods for cleaning teeth.

BACKGROUND

Regular self-administered oral care is an important part of maintaining the condition of teeth and gums. Recommendations for teeth brushing, for example, call for performing the activity multiple times per day, both for adults and children. All too often, however, teeth brushing is performed below recommended standards, e.g., for less than a recommended time interval, less than a suggested number of times per day, or without sufficiently cleaning all teeth. Reasons for not performing teeth brushing to recommended standards can include, for example, time and effort required to satisfactorily clean all teeth in the top and bottom jaw, user boredom during the activity, and lack of interest in performing a chore-like activity that is not fun and engaging (the latter concern can be particularly powerful for young children).

Attempts to address the above-mentioned and other issues regarding teeth brushing have produced a number of variations on the traditional tooth brush design. For example, electrically-actuated toothbrushes in conventional form (i.e., a long cylindrical device with a small bristled head for cleaning a small subset of teeth at any time) are common to aid teeth brushing effectiveness. In addition, alternative tooth brush designs exist, such as mouthpieces with bristled surfaces that attempt to clean all of a user's teeth at one time.

However, there are a number of drawbacks associated with existing devices. For example, conventional toothbrushes and equivalent electrically actuated toothbrushes still require a user to hold and manipulate the toothbrush by hand to clean all teeth. The bristled head of these brushes can clean only a couple teeth at any one time. Teeth brushing mouthpiece designs can clean all teeth at once, but are often complex devices that are expensive to manufacture and can break easily. For example, certain devices utilize mouthpieces with channels that surround teeth on three sides that all have bristles attached thereto. Forming such a mouthpiece and attaching bristles to such a complex shape can be challenging and expensive. In other examples, complex mechanisms for actuating bristles are included, such as individual rotating bristle bunches, or groups of bristles that translate back and forth via a rod or other driving linkage. Moreover, even when mouthpiece designs are utilized, they often are configured to couple to a handheld battery and/or control component that is held by a user for the duration of the teeth cleaning. Finally, none of the prior art devices provide any features that aid in engaging a user during the tooth brushing activity, so as to mitigate boredom and provide a positive incentive for performing the activity.

Accordingly, there is a need for improved oral care devices and methods that provide hands-free, efficient, and effective cleaning of teeth. Further, there is a need for such improved devices that also provide a mechanism for engaging users during teeth brushing.

SUMMARY

The present disclosure generally provides an oral care device and method that can be actuated by a user's bite rather than by hand, tongue, or other manipulation. The devices and methods described herein can also effectively clean all teeth at once, thereby reducing the amount of time and effort required to thoroughly brush teeth. In general, the devices described herein utilize a generally U-shaped mouthpiece configured to be received in a user's mouth. Bristles formed on the mouthpiece contact a user's upper and lower teeth simultaneously. The devices described herein also include a housing configured to be largely disposed outside the user's mouth and house a battery and actuator for vibrating the device. A pressure-sensitive switch can be positioned such that a user's bite force on the mouthpiece can be detected and utilized to selectively power the actuator. As a result, a user can control teeth brushing with the device by simply biting down on the mouthpiece. Further, at least a portion of the housing configured to remain outside the user's mouth can include a surface configured to receive a decorative decal thereon. The surface can be located, for example, substantially in front of a user's mouth and the decorative decals can include, for example, an illustration of lips, a smile, etc. The unique mode of operation of the device, in combination with the decorative decals, can aid in engaging users during teeth brushing, thereby encouraging them to perform teeth brushing more frequently.

In one aspect, an oral care device is provided that includes a mouthpiece configured to be received within a mouth of a user. The mouthpiece can include an upper bristle track having a plurality of bristles extending from an upper surface thereof and a lower bristle track having a plurality of bristles extending from a lower surface thereof. The upper bristle track and the lower bristle track can be pivotably coupled to one another. The device can further include a first housing component coupled to the mouthpiece such that at least a portion of the first housing component is disposed between the upper bristle track and the lower bristle track and can be compressed therebetween when the upper bristle track and the lower bristle track pivotably move relative to one another. The device further includes a second housing component sealingly coupled to the first housing component to define a watertight cavity between the first and second housing components. The device also includes a battery disposed within the cavity, an actuator disposed within the cavity and coupled to the battery, and a pressure sensitive switch disposed within the cavity. The pressure sensitive switch can be effective to detect pressure exerted on the first housing component when the upper and lower bristle tracks pivotably move relative to one another and selectively couple the actuator to the battery.

The devices and methods described herein can have a number of additional features and/or variations, all of which are within the scope of the present disclosure. In some embodiments, for example, at least the second housing component can be positioned outside the mouth of a user when the mouthpiece is within the mouth of the user. In some embodiments, the actuator can be configured to vibrate the mouthpiece and, in some embodiments, can comprise a rotary motor spinning an eccentric mass.

The second housing can, in some embodiments, include a surface configured to receive a decorative decal. The surface can have a variety of shapes but, in some embodiments, can have an oval shape and can be flat. Any of a variety of other shapes are also possible. For example, in some embodiments the surface can have a curved shape generally approximating a set of lips.

In some embodiments, the first housing component and the second housing component can be coupled together via an interference fit and a sealing element can be disposed therebetween. The sealing element can, in some embodiments, be an O-ring. In other embodiments, a sealant such as a glue can be utilized.

The first housing component and the second housing component can be coupled together in a variety of manners. For example, in some embodiments the first housing component and the second housing component can be coupled together via sonic welding.

The first housing component and the second housing component can be formed from a variety of materials and, in some embodiments, can be over-molded with a polymer material, such as a thermoplastic polyurethane in certain embodiments.

In another aspect, an oral care method is provided that can include inserting a mouthpiece of an oral care device into a user's mouth such that a portion of the device containing a battery and an actuator remain outside the user's mouth. The method can further include applying bite force to the mouthpiece within the user's mouth to actuate a pressure-sensitive switch that selectively couples the actuator to the battery to vibrate the device, and selectively controlling vibration of the mouthpiece using bite force.

In some embodiments, inserting the mouthpiece into the user's mouth can include contacting a plurality of a user's teeth with bristles extending from the mouthpiece. The bristles can simultaneously contact a plurality of a user's teeth on both the upper and lower jaw in some embodiments. In other embodiments, the method can further include affixing a decorative decal to a surface of the device that remains outside of a user's mouth.

In some embodiments, variation in bite force can be linearly related to variation in vibration imparted by the actuator. In certain embodiments, the method can further include releasing bite force on the mouthpiece to electrically decouple the actuator from the battery, and removing the mouthpiece from the user's mouth.

Any of the features or variations described above can be applied to any particular aspect or embodiment of the disclosure in a number of different combinations. The absence of explicit recitation of any particular combination is due solely to the avoidance of repetition in this summary.

BRIEF DESCRIPTION OF THE DRAWINGS

The aspects and embodiments of the invention described above will be more fully understood from the following detailed description taken in conjunction with the accompanying drawings, in which.

DETAILED DESCRIPTION

Certain exemplary embodiments will now be described to provide an overall understanding of the principles of the devices and methods disclosed herein. One or more examples of these embodiments are depicted in the accompanying figures. Those skilled in the art will understand that the devices and methods specifically described herein and depicted in the accompanying figures are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

The present invention generally provides an oral care device and method that can be actuated by a user's bite rather than by hand, tongue, or other manipulation. The devices and methods described herein can also effectively clean all teeth at once, thereby reducing the amount of time and effort required to thoroughly brush teeth. In general, the devices described herein utilize a generally U-shaped mouthpiece configured to be received in a user's mouth. Bristles formed on the mouthpiece contact a user's upper and lower teeth simultaneously. The devices described herein also include a housing configured to be largely disposed outside the user's mouth and house a battery and actuator for vibrating the device. A pressure-sensitive switch can be positioned such that a user's bite force on the mouthpiece can be detected and utilized to selectively power the actuator. As a result, a user can control teeth brushing with the device by simply biting down on the mouthpiece. Further, at least a portion of the housing configured to remain outside the user's mouth can include a surface configured to receive a decorative decal thereon. The surface can be located, for example, substantially in front of a user's mouth and the decorative decals can include, for example, an illustration of lips, a smile, etc. The unique mode of operation of the device, in combination with the decorative decals, can aid in engaging users during teeth brushing, thereby encouraging them to perform teeth brushing more frequently.

FIGS. 1-4 illustrate one embodiment of an oral care device according to the teachings of the present invention. The device 100 includes a mouthpiece 102, first housing component 104, and second housing component 106. The mouthpiece 102 can be configured to be received within a user's mouth during use, while the first and second housing components 104, 106 can be configured to remain substantially outside a user's mouth during use (as is discussed in more detail below, at least a portion of the first housing component 104 can be configured to overlap with a portion of the mouthpiece 102 and may extend into a user's mouth).

The mouthpiece 102 is generally U-shaped to match the shape of teeth in the upper and lower jaws. The mouthpiece 102 can include an upper bristle track 108 and a lower bristle track 110. The upper bristle track 108 can include a plurality of bristles 112 extending from an upper surface thereof, such that the bristles 112 can contact the teeth of the upper jaw when the upper bristle track 108 is positioned in a user's mouth just below the upper teeth. Similarly, the lower bristle track 110 can include a plurality of bristles 114 that extend from a lower surface thereof, such that the bristles 114 can contact the teeth of the lower jaw when the lower bristle track 110 is positioned in a user's mouth just above the lower teeth.

The upper and lower bristle tracks 108, 110 can have a substantially flat profile, such that all bristles 112, 114 extend from a single planar surface and extend in a same direction (e.g., vertically). This can simplify manufacturing and reduce the cost of the device. In other embodiments, however, the upper and lower bristle tracks 108. 110 can have curved concave or convex shapes that allow various bristles 112, 114 to extend at different angles. For example, in some embodiments the upper or lower bristle track can have a concave, generally U-shaped profile in cross-section, and bristles can extend from all three inner surfaces of the U-shaped profile to contact teeth received therein from multiple angles.

The upper and lower bristle tracks 108, 110 can be coupled to one another in certain embodiments. For example, the upper and lower bristle tracks 108, 110 can be pivotably coupled to one another in a manner similar to the upper and lower jaws of the mouth, i.e., via a pivoting connection at the proximal end of the mouthpiece. In the embodiment shown in FIG. 1, connecting portions 116, 118 serve to couple the upper and lower bristle tracks 108, 110 in a manner that permits pivoting motion therebetween. Accordingly, when a user places the mouthpiece 102 in their mouth and bites down on the upper and lower bristle tracks 108, 110, they can pivot relative to one another about an axis extending through the connecting portions 116, 118. The connecting portions 116, 118 can be formed in a variety of manners. For example, the connection portions 116, 118 can be hinge components that connect upper and lower bristle tracks 108, 110, or they can be formed from a curved portion of the material that forms the upper and lower bristle tracks 108, 110.

At a distal end of the mouthpiece, a proximal portion of the first housing component 104 can be positioned between the upper and lower bristle tracks 108, 110. As a result, the proximal portion of the first housing component 104 can be compressed when a user bites down on the upper and lower bristle tracks 108, 110. As is explained in more detail below, compressing the proximal portion of the first housing component 104 can activate a pressure sensitive switch located within the first housing component and cause an actuator to vibrate the entire device 100, thereby causing the bristles 112, 114 to move relative to a user's teeth. Moving the bristles 112, 114 relative to the user's teeth can clean the teeth and cause any toothpaste applied to the bristles to foam and aid in cleaning. To stop the device from vibrating, a user need only release the bite force on the upper and lower bristle tracks 108, 110 to remove the compressive force exerted on the proximal portion of the first housing component 104 that is disposed therebetween. Further, the force of vibration can be linearly or otherwise related to the bite force applied by the user, thereby allowing the user to easily control the force of brushing action using their bite.

A second housing component 106 can be coupled to the first housing component 104 at a distal end thereof. The second housing component 106 can, in some embodiments, form a cap that seals off a cavity within the first housing component 104 and protects the actuator, pressure sensitive switch, battery, or other components disposed within the cavity from exposure to water, toothpaste, or other elements of the environment. In some embodiments, the second housing component 106 can be permanently sealed to the first housing component 104 such that a user cannot access the cavity without destroying the device. Such a configuration can be used, for example, to ensure that young children cannot access the internals of the device 100. Sealing of the first and second housing components 104, 106 can be accomplished in a variety of manners, including, for example, the use of adhesives or a welding process, such as sonic welding.

The second housing component 106 can include a surface 120 at a distal end thereof that can be configured to receive a decorative decal thereon. The surface can be configured to approximately align with a user's mouth when the mouthpiece 102 is received within the mouth. As a result, the surface 120 can be positioned immediately in front of a user's mouth when viewed from in front of a user (e.g., by a person standing in front of the user, or by a user herself when standing in front of a mirror). The surface 120 can have a variety of two-dimensional shapes, including, for example, an oval shape, a rectangular shape, etc. The surface can also have a variety of three-dimensional profiles, including flat, curved, etc. In some embodiments, the surface 120 can have a shape approximating the shape of a pair of lips. Further, the surface can be flat, substantially flat, or can have any of a variety of different curved profiles.

Figure 1:
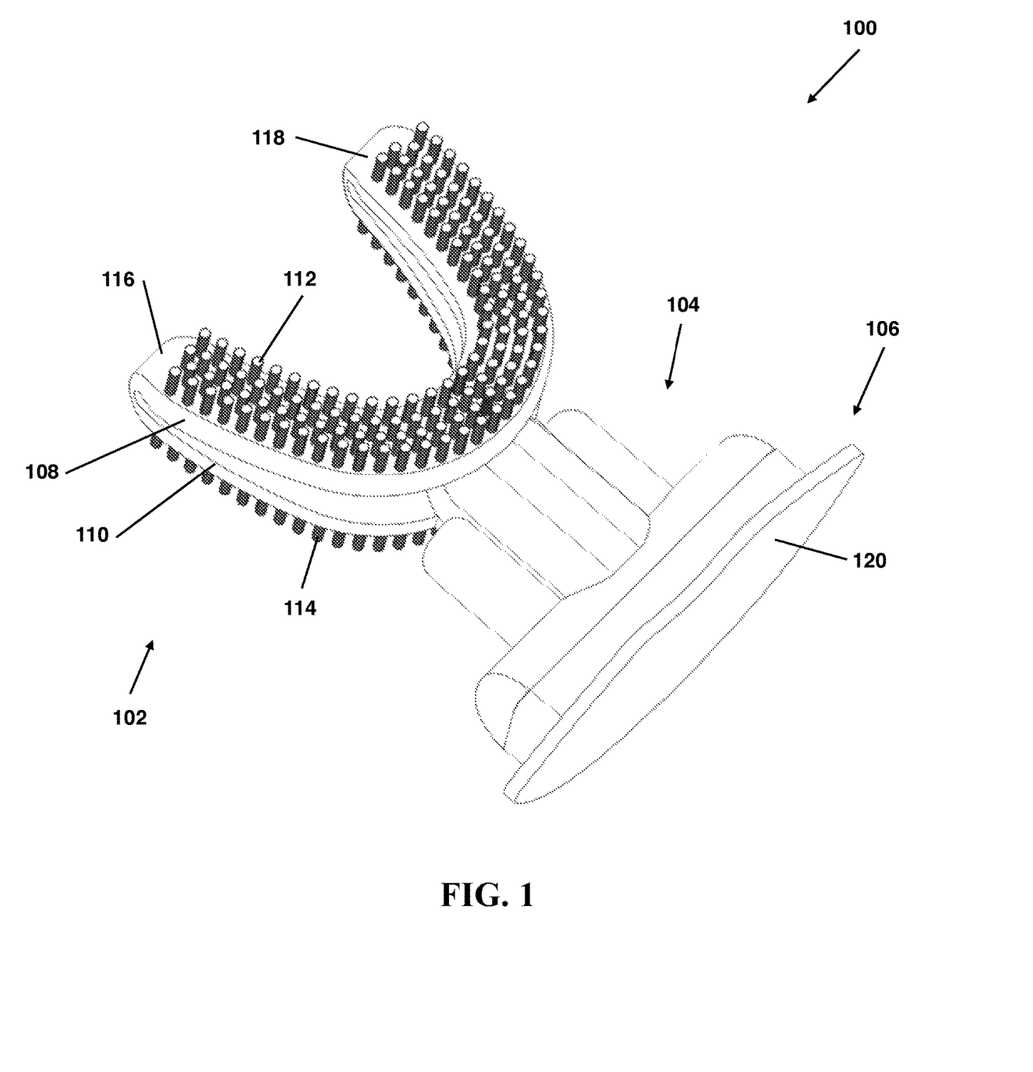
FIG. 1 is a perspective view illustration of one embodiment of an oral care device.
Figure 2:
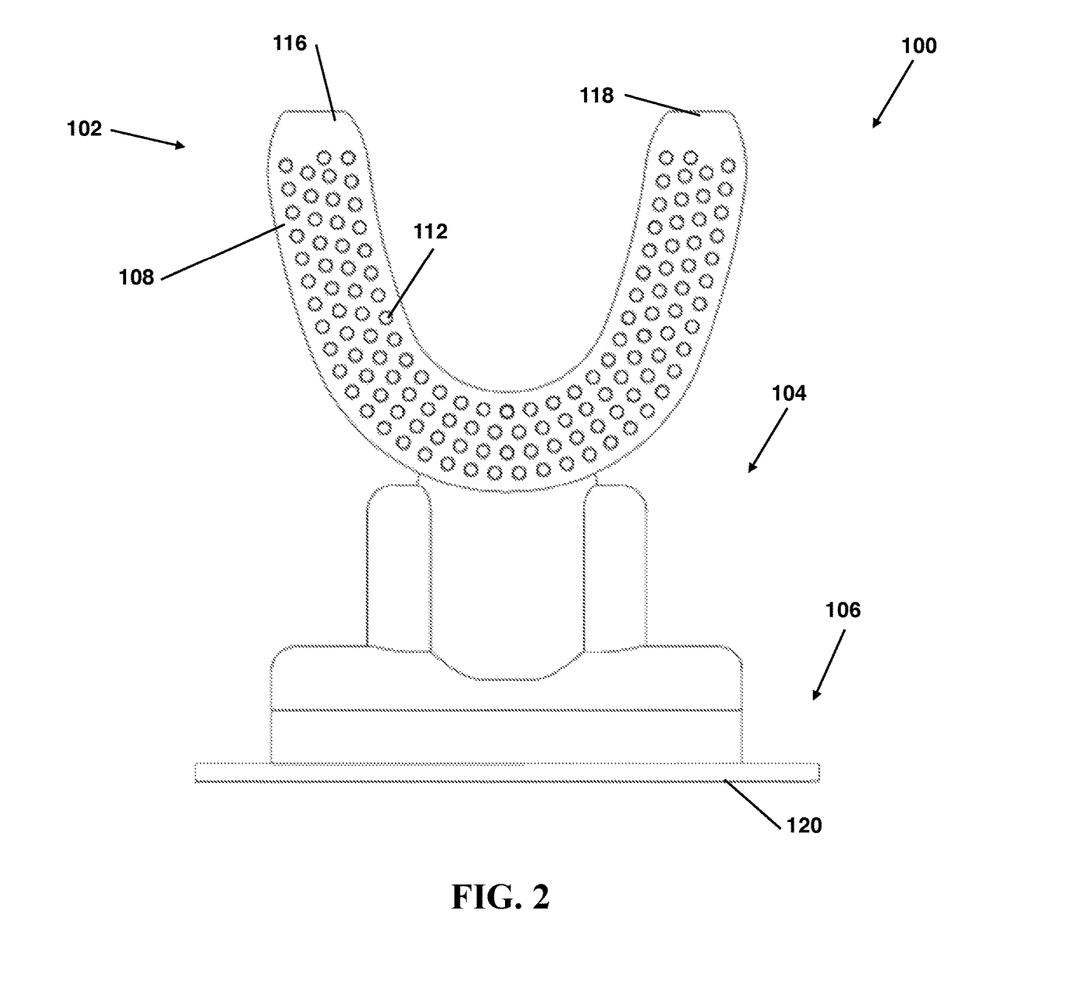
FIG. 2 is a top view of the device of FIG. 1.

In some embodiments, a user can place a decorative decal (not shown) on the surface 120. The decal can have any of a number of illustrations thereon, including, for example, a set of lips, a smile, a tongue, etc. The decal can serve to personalize the device 100 for a particular user, and to help differentiate one user's device from another user's device when they are located near one another. Further, the decorative decal can help engage and entertain users, including young children, while they are using the device 100 to brush their teeth. Decorative decals can be formed on a waterproof substrate material, such as a polypropylene film, that can be exposed to water and can be removed from the surface 120 if desired (e.g., to swap out for another decal, relocate to a new device, etc.).

Figure 3:
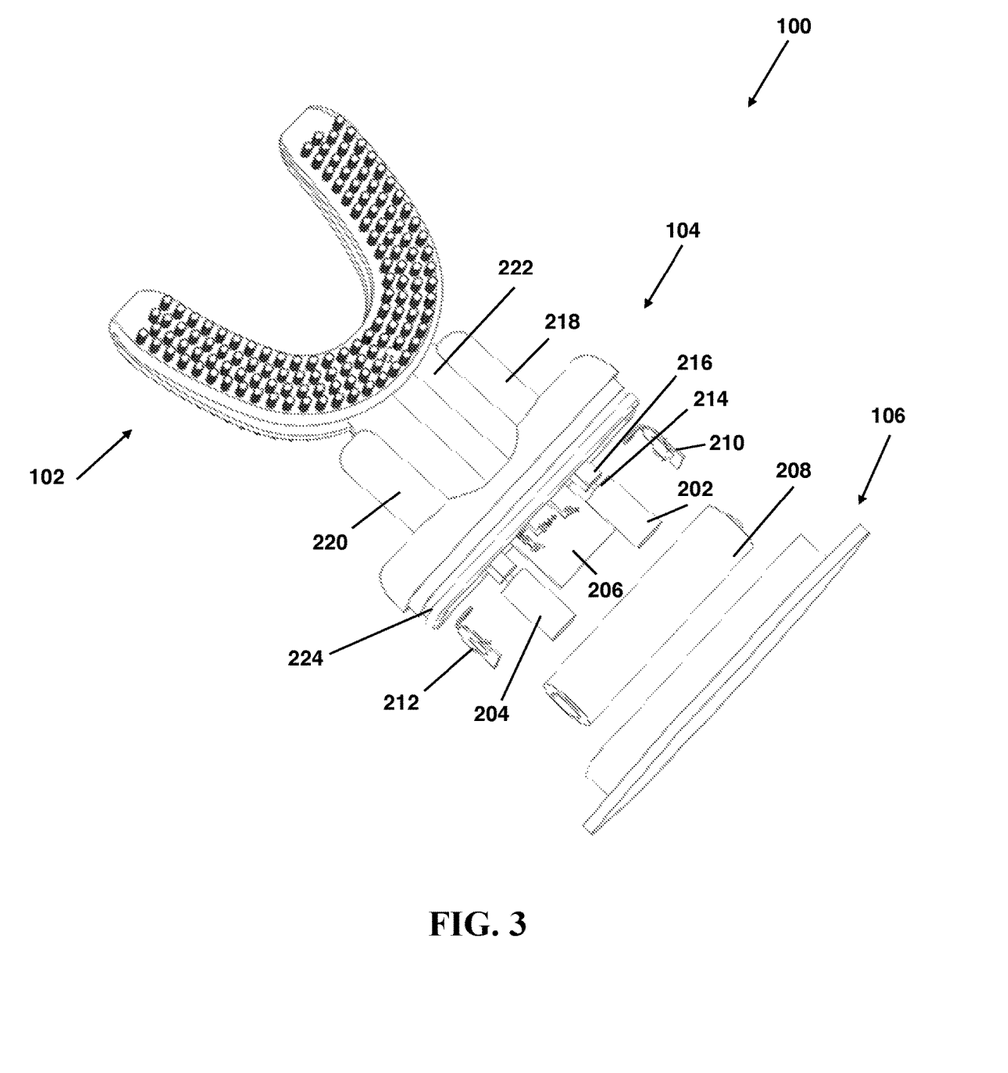
FIG. 3 is a perspective exploded view illustration of the device of FIG. 1.
Figure 4:
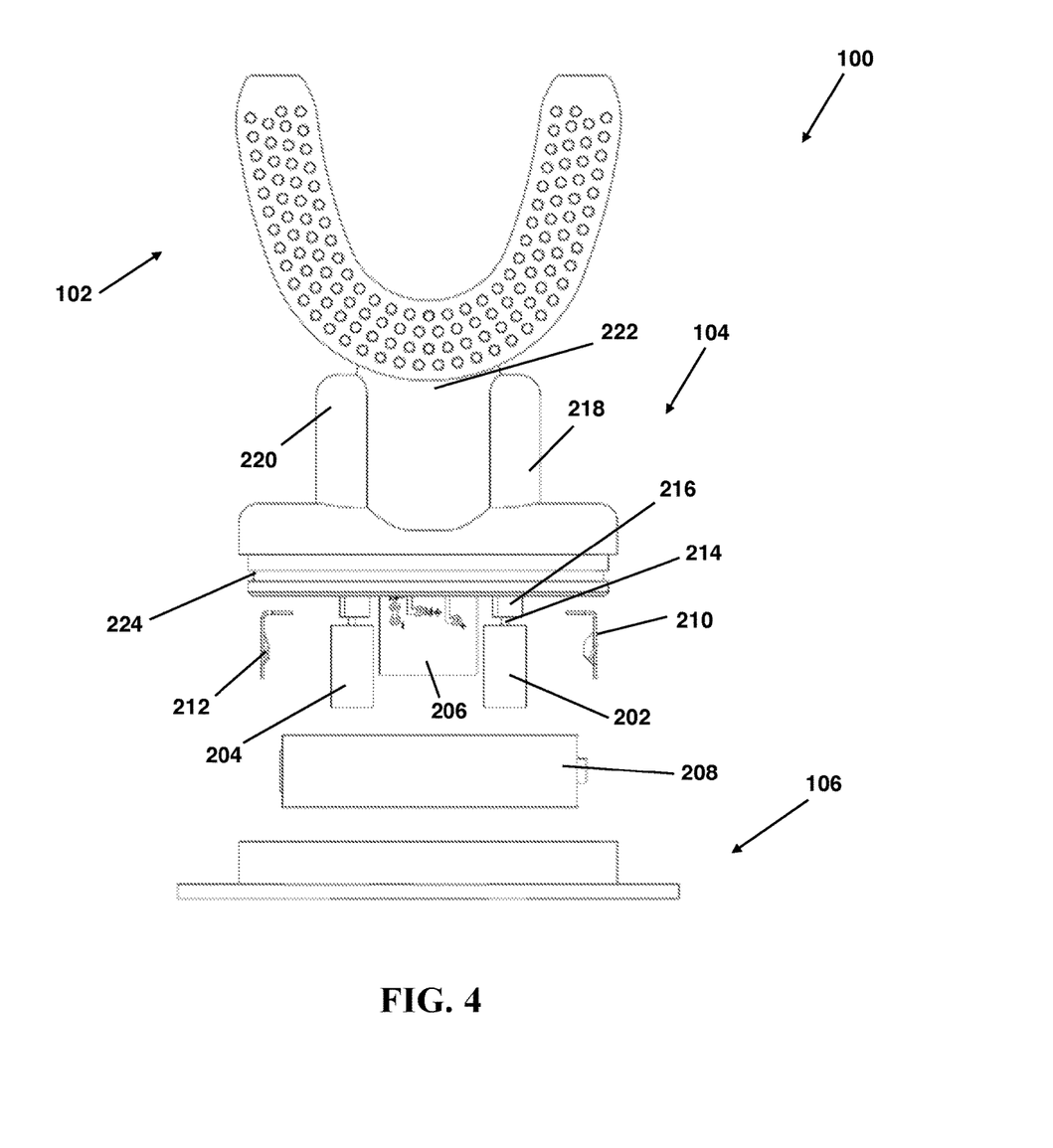
FIG. 4 is a top exploded view of the device of FIG. 1.

FIGS. 3 and 4 show an exploded view of the device 100 that exposes components typically sealed within the cavity formed between the first and second housing components 104, 106. As shown in the figures, the device 100 includes a first actuator 202, a second actuator 204, a printed circuit board 206, and a battery 208 that are sealed between the first and second housing components 104, 106. The first and second actuators 202, 204 can be coupled to the printed circuit board 206 via electrical leads (not shown), and the battery 208 can also be coupled to the printed circuit board 206 via a positive battery connector 210 and a negative battery connector 212 that may themselves be coupled to the printed circuit board 206 via other electrical leads (not shown). In another embodiment, actuator 202 can be soldered or otherwise electrically connected to battery connector 210, while actuator 204 can be soldered or otherwise electrically connected to battery connector 212. A second lead from each actuator 202, 204 can be electrically connected to the printed circuit board 206 such that a pressure sensitive switch on the printed circuit board can connect the two leads when actuated. This connection can complete an electrical circuit running from the battery through both actuators 202, 204, thereby vibrating the device 100. In still another embodiment, one electrical lead from each actuator motor 202, 204 can be soldered to a contact that is also connected to one terminal of the battery 208. A second electrical lead from each actuator motor 202, 204 can be soldered to a second contact, and a third contact can be electrically connected to the second terminal of the battery 208. The pressure sensitive switch can be configured to electrically connect the second and third contacts when actuated, such that an electrical circuit is completed between the battery and each actuator motor 202, 204 when the pressure sensitive switch is actuated.

The first and second actuators 202, 204 can be any of a variety of components capable of vibrating the device 100. In the illustrated embodiment, the first and second actuators 202, 204 are each direct current (DC) rotary motors that spin a shaft 214 with an eccentric mass 216 mounted thereon. When the eccentric mass is rotated, it creates a shifting force that tends to induce vibration of the device 100. Other types of vibration actuators can also be employed, including, for example, motors that translate a mass forward and backward, etc.

A safety feature of the device 100 is that the battery 208 and actuators 202, 204 are located outside of a user's mouth and only the mouthpiece is received within the mouth. Further, there are no complicated moving parts (e.g., sliding racks of bristles, rotating bristle bunches, etc.) located within the user's mouth or associated drive rods or other mechanisms to connect the actuators and such moving parts. Rather, the device 100 is actuated by vibration induced from the actuators 202, 204 that are sealed within the housing cavity and cause the entire device 100 to vibrate. In order to maximize the transfer of actuator force to the mouthpiece, it can be desirable to position the actuators 202, 204 (and, in particular, the spinning eccentric mass 216 of each actuator) as close to the mouthpiece 102 as possible. Accordingly, the first housing component 104 can include a first housing tube 218 and a second housing tube 220 that extend toward the mouthpiece 102 and are configured to receive an actuator therewithin (i.e., the actuators 202, 204 shown in FIG. 3 can be translated proximally toward the mouthpiece 102 into the housing tubes 218, 220).

The first housing component 104 also includes a central portion 222 that extends between the housing tubes 218, 220. A proximal end portion of the central portion 222 can extend into the space between the upper and lower bristle tracks 108, 110 and can be coupled to at least one of the upper and lower bristle tracks. A cavity within the central portion 222 can house the printed circuit board 206. As noted above, the printed circuit board 206 can be electrically coupled to the battery 208 and each of the actuators 202, 204. A pressure sensitive switch (not shown) can be disposed on the printed circuit board 206 and configured to selectively connect the actuators 202, 204 to the battery 208. Further, the pressure sensitive switch can be disposed on a portion of the printed circuit board 206 that sits between the upper and lower bristle tracks 108, 110 in a proximal end of the cavity of the central portion 222. As a result, when a user bites down on the upper and lower bristle tracks 108, 110, the tracks can compress the proximal end portion of the central portion 222 and activate the pressure sensitive switch, thereby connecting the actuators 202, 204 to the battery 208 and vibrating the device 100. It should be appreciated that in some embodiments the pressure sensitive switch can be a separate component from the printed circuit board 206 rather than formed thereon.

As mentioned above, the first and second housing components 104, 106 cooperate to seal the actuators 202, 204, printed circuit board 206, battery 208, and other internal components from exposure to water or other external elements. The first and second housing components 104, 106 can be configured to fit together using, for example, an interference fit. In addition, a sealing element (not shown) can be placed between the first and second housing components 104, 106 to aid in sealing the inner cavity from the environment. For example, in some embodiments an O-ring or other sealing element can be placed within a groove 224 formed around an outer circumference of the first housing component 104. When the first housing component 104 and the second housing component 106 are mated together following installation of the actuators 202, 204, printed circuit board 206, battery 208, and other internal components, the O-ring can be trapped between the two housing components and prevent water ingress.

In addition to the above-mentioned O-ring or other sealing element, the first and second housing components can be secured together using any number of methods that can aid in preventing their disassembly or the ingress of foreign material, such as water. For example, a glue or other adhesive can be used to join the first and second housing components 104, 106 together and seal any seam formed therebetween. Further, in some embodiments the two housing components can be welded or otherwise permanently joined together. In some embodiments, for example, sonic welding can be used to permanently join and seal the first and second housing components 104, 106 with one another.

The device 100 can be formed from a variety of materials. For example, the device 100 can be formed from biocompatible metals such as stainless steel, titanium, etc. However, in other embodiments any of a variety of polymer materials can be used to form the various components of the device 100. For example, the upper and lower bristle tracks 108, 110 can be formed from a semi-rigid polymer material such as polypropylene and bristles 112, 114 can be formed from nylon, such as nylon products manufactured by DuPont™. The first and second housing components 104, 106 can be formed from rigid materials, such as polypropylene. However, a proximal portion of the first housing component 104 that extends between the upper and lower bristle tracks 108, 110 and houses the pressure sensitive switch can be formed from a semi-rigid material, such as a soft thermoplastic polyurethane. This can allow the first housing component to deform in the area of the pressure sensitive switch as the upper and lower bristle tracks 108, 110 move relative to one another and compress the first housing component 104. Further, in some embodiments the device 100, or at least the first and second housing components 104, 106, can be over molded with a thermoplastic polyurethane (TPU), such as a Food and Drug Administration (FDA) approved food grade TPU, to aid in resisting water ingress and bacteria growth.

A method of using the device 100 enables a user to brush all of her teeth simultaneously in a hands-free manner. For example, a user can take the device 100 and, if desired, apply a decorative decal to the surface 120 on the distal end of the second housing component 106. The user can also apply toothpaste to the bristles 112, 114 of upper and lower bristle tracks 108, 110. The user can then insert the mouthpiece 102 such that the upper and lower bristle tracks 108, 110 align with the user's teeth (i.e., the generally U-shaped bristle tracks align with the generally U-shaped arrangement of teeth in the upper and lower jaw). The user can then activate the device 100 by simply biting down on the mouthpiece 102, which will cause the upper and lower bristle tracks 108, 110 to pivot about the connecting portions 116, 118 and compress the portion of the first housing component 104 that is disposed between the upper and lower bristle tracks 108, 110. This compression can actuate the pressure sensitive switch positioned within the cavity of the first housing component 104, thereby electrically coupling the battery 208 to the actuators 202, 204. The user can selectively control the vibration of the device 100 using bite force and, in some embodiments, the pressure sensitive switch can be configured to smoothly vary vibration level with pressure, such that a user can induce gentle vibration with a light bite and stronger vibration with a stronger bite. Note that the user's hands are free to perform other tasks during teeth cleaning.

When the user is finished with teeth cleaning, any bite force on the upper and lower bristle tracks 108, 110 can be released to deactivate the actuators 202, 204. The mouthpiece 102 can be removed from the user's mouth and the device can be rinsed in preparation for a subsequent use.

All papers and publications cited herein are hereby incorporated by reference in their entirety. The present invention is not to be limited in scope by the examples provided herein, since the examples are intended as illustrations of one or more aspects of the invention and other functionally equivalent embodiments are within the scope of the invention. Furthermore, one skilled in the art will appreciate additional features and advantages of the invention based on the above-described embodiments. Accordingly, the invention is not to be limited by what has been particularly shown and described, except as indicated by the appended claims.

Still further, the terms "a" and "an" are used interchangeably above, and are equivalent to the phrase "one or more" as utilized in the present application. The terms "comprising," "having," "including," and "containing" are to be construed as open-ended terms (i.e., meaning "including, but not limited to,") unless otherwise noted above. The terms "about" and "approximately" used for any numerical values or ranges indicate a suitable dimensional tolerance that allows the composition, part, or collection of elements to function for its intended purpose as described herein. These terms generally indicate a ±10% variation about a central value. The recitation of any ranges of values herein is merely intended to serve as a shorthand method of referring individually to each separate value falling within the range, unless otherwise indicated herein, and each separate value is incorporated into the specification as if it were individually recited. To the extent that linear or circular dimensions are used in the description of the disclosed devices and methods, such dimensions are not intended to limit the types of shapes that can be used in conjunction with such devices and methods. A person skilled in the art will recognize that an equivalent to such linear and circular dimensions can easily be determined for any geometric shape. All methods described herein can be performed in any suitable order unless otherwise indicated herein or otherwise clearly contradicted by context. The use of any and all examples, or exemplary language (e.g., "such as"), provided herein is intended merely to better illuminate the invention and does not impose a limitation on the scope of the invention unless otherwise claimed. No language in the specification should be construed as indicating any non-claimed element as essential to the practice of the invention.

What is claimed is:

1. An oral care device, comprising:
    a mouthpiece configured to be received within a mouth of a user, the mouthpiece including an upper bristle track having a plurality of bristles extending from an upper surface thereof and a lower bristle track having a plurality of bristles extending from a lower surface thereof, wherein the upper bristle track and the lower bristle track are pivotably coupled to one another;
    a first housing component coupled to the mouthpiece such that at least a portion of the first housing component is disposed between the upper bristle track and the lower bristle track and can be compressed therebetween when the upper bristle track and the lower bristle track pivotably move relative to one another;
    a second housing component sealingly coupled to the first housing component to define a watertight cavity between the first and second housing components;
    a battery disposed within the cavity;
    an actuator disposed within the cavity and coupled to the battery; and
    a pressure sensitive switch disposed within the cavity and effective to detect pressure exerted on the first housing component when the upper and lower bristle tracks pivotably move relative to one another and selectively couple the actuator to the battery,
    wherein the first housing component and the second housing component are coupled together via an interference fit and a sealing element is disposed therebetween.

2. The oral care device of claim 1, wherein at least the second housing component is positioned outside the mouth of a user when the mouthpiece is within the mouth of the user.

3. The oral care device of claim 1, wherein the actuator vibrates the mouthpiece.

4. The oral care device of claim 3, wherein the actuator comprises a rotary motor spinning an eccentric mass.

5. The oral care device of claim 1, wherein the sealing element is an o-ring.

6. The oral care device of claim 1, wherein the first housing component and the second housing component are coupled together via sonic welding.

\* \* \* \* \*